(12) United States Patent
Hayashizaki et al.

(10) Patent No.: US 6,517,696 B1
(45) Date of Patent: Feb. 11, 2003

(54) CAPILLARY ELECTROPHORETIC APPARATUS, SAMPLE PLATE AND SAMPLE INJECTION METHOD

(75) Inventors: Yoshihide Hayashizaki, Ibaraki (JP); Shin Nakamura, Kyoto (JP); Makoto Hazama, Kyoto (JP); Hideshi Fujiwake, Kyoto (JP)

(73) Assignees: The Institute of Physical and Chemical Research, Saitama (JP); Shimadzu Corporation, Kyoto (JP); Japan Science and Technology Corporation, Saitama (JP)

( * ) Notice: Subject to any disclaimer, the term of this patent is extended or adjusted under 35 U.S.C. 154(b) by 0 days.

(21) Appl. No.: 09/426,760

(22) Filed: Oct. 26, 1999

(30) Foreign Application Priority Data

Nov. 2, 1998 (JP) .......... 10-311674
Nov. 2, 1998 (JP) .......... 10-311675
Nov. 30, 1998 (JP) .......... 10-338896

(51) Int. Cl.[7] .......... C25B 9/00; G01N 27/27; G01N 27/403; G01N 27/453
(52) U.S. Cl. .......... 204/604; 422/99; 422/102
(58) Field of Search .......... 422/99, 102; 204/601

(56) References Cited

U.S. PATENT DOCUMENTS

| 4,735,778 A | * | 4/1988 | Maruyama et al. | 422/102 |
|---|---|---|---|---|
| 5,384,024 A | * | 1/1995 | Moring et al. | 204/602 |
| 5,439,578 A | * | 8/1995 | Dovichi et al. | 204/603 |
| 5,560,811 A | * | 10/1996 | Briggs et al. | 204/451 |
| 5,968,331 A | * | 10/1999 | Kambara et al. | 204/450 |
| 6,068,752 A | * | 5/2000 | Dubrow et al. | 204/450 |
| 6,093,300 A | * | 7/2000 | Hayashizaki et al. | 204/451 |
| 6,241,949 B1 | * | 6/2001 | Kane | 422/100 |
| 6,325,908 B1 | * | 12/2001 | Imai et al. | 204/451 |
| 6,358,387 B1 | * | 3/2002 | Kopf-Sill et al. | 204/602 |

FOREIGN PATENT DOCUMENTS

| EP | 10206382 | 8/1998 |
|---|---|---|
| EP | 0 864 860 A1 | 9/1998 |
| EP | 11064277 | 3/1999 |

* cited by examiner

*Primary Examiner*—Jili Warden
*Assistant Examiner*—Jennine M. Brown
(74) *Attorney, Agent, or Firm*—Rader, Fishman & Grauer PLLC (57) ABSTRACT

An electrode plate of a sample plate is set on the body of an electrophoretic apparatus, while a plug is inserted into a migration high voltage line connection hole and connected to a high-tension distribution cable. Each well of a base plate is inserted into a through hole of a well guide and further press-fit and engaged into a cavity of an electrode plate, for fixing the base plate to the electrode plate. Thereafter a sample is introduced into each well of the base plate and an end of a capillary column is dipped into each well for applying a migration voltage and electrophoretically injecting the sample into the capillary column.

4 Claims, 7 Drawing Sheets

CAPILLARY ELECTROPHORETIC APPARATUS, SAMPLE PLATE AND SAMPLE INJECTION METHOD

BACKGROUND OF THE INVENTION

1. Field of the Invention

The present invention relates to a capillary electrophoretic apparatus comprising a capillary electrophoretic part electrophoresing a sample injected into an end of a capillary column and detection means detecting each component separated in the capillary column at an appropriate position of the capillary column, and inclusively, it relates to a method and an apparatus characterized in sample injection into a capillary column.

2. Description of the Prior Art

Besides having those that comprise a single capillary column, capillary electrophoretic apparatuses also have a multi-capillary electrophoretic apparatus comprising a multi-capillary array migration part including a plurality of capillary columns for injecting a plurality of samples one by one into the capillary columns and simultaneously electrophoresing the samples in all capillary columns and an optical measuring part irradiating the capillary columns with light in the multi-capillary array migration part for measuring absorbance by the samples on the irradiated portion or fluorescence from the samples.

The capillary columns include those charged and not charged with gels for migration.

A capillary electrophoretic apparatus is applied for the separation of protein, and sequence determination for DNA. When applied to sequence determination for DNA, the capillary electrophoretic apparatus employs Sanger's reaction, electrophoreses a DNA fragment sample prepared by labeling a primer or a terminator with a fluorescent material and detects fluorescence from the DNA fragment sample during migration for determining the base sequence.

A DNA sequencer having high sensitivity, a high speed and high throughput is necessary for sequence determination for DNA having long base sequence such as a human genome. As one method, a multi-capillary DNA sequencer prepared by arranging a plurality of capillary columns in place of that employing a flat plate type slab gel is proposed. With such a capillary column, a sample can not only be readily handled or injected but also migrated at a high speed and detected in high sensitivity, when compared to the slab gel. If a high voltage is applied to the slab gel, a band is spread or a temperature gradient is caused due to influence by Joulean heat However, the capillary column hardly causes such problems and can perform detection in high sensitivity with small band spreading even if performing high-speed migration with application of a high voltage.

In capillary electrophoresis, a sample is injected into a capillary column under pressure or with application of a voltage. A method of electrophoretically injecting a sample is widely employed in general due to the simplicity of the apparatus structure, easiness of operations and excellent controllability of parameters.

In relation to the method of injecting the sample into the capillary column, migrational separability in later migrational separation must not be deteriorated and sample injection must be simpler.

Whether the capillary column is charged with a gel or not, one end of the capillary column must be dipped in a prepared sample, the other end must be dipped in a buffer solution, and an electrode such as a platinum wire must be dipped in the vicinity of the end of the capillary column within the sample. In a structure holding the electrode in the vicinity of the end of each capillary column in electrophoretic sample injection, the electrode structure for sample injection becomes complicated in the case of a multi-capillary electrophoretic apparatus collectively arranging a plurality of capillary columns in the form of an array for simultaneously performing electrophoresis. After dipping the end of the capillary column in a sample contained in a sample injection container and performing injection by applying a voltage or the like, the end of the capillary column must be transferred into a reservoir containing a buffer solution for migration. Thus, operations between sample injection and the start of migration are troublesome, and it is convenient if the operations can be automated.

Figure 4:
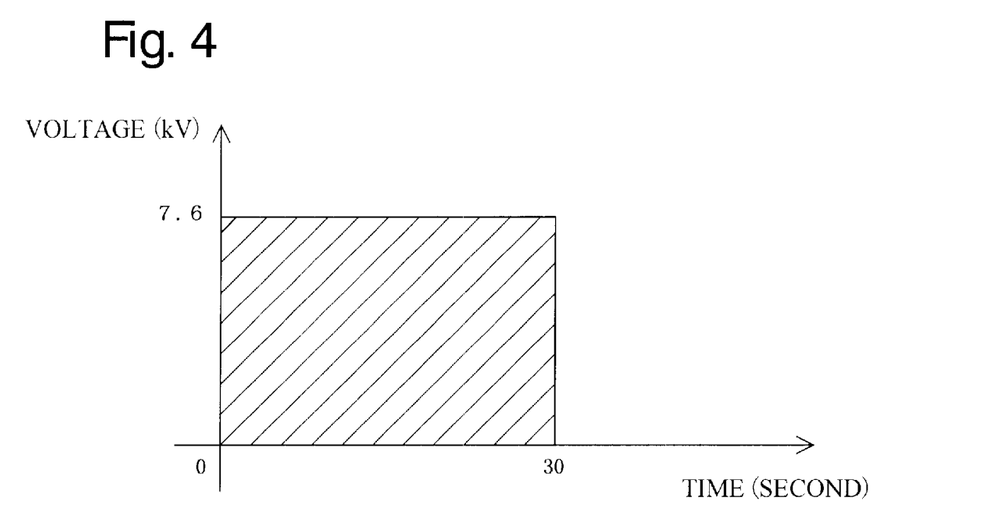
FIG. 4 illustrates examples of a voltage applied in conventional sample injection in a capillary electrophoretic apparatus and time, with the vertical and horizontal axes showing the voltage (kV) and the time (sec.) respectively.

In both of an electrophoretic apparatus comprising a single capillary column and a multi-capillary electrophoretic apparatus, migrational separability may be deteriorated in capillary electrophoresis charged with a gel, depending on the sample injection method. In the case of electrophoretically injecting a sample, a prescribed high voltage is applied within several seconds when starting voltage application and the high voltage is zeroed within several seconds when finishing voltage application in a conventional voltage application method, as shown in FIG. 4. Referring to FIG. 4, the vertical axis shows the voltage (kV) and the horizontal axis shows the time (second). In this example, a voltage of 7.6 kV is applied for 30 seconds. However, If a high voltage is applied to the capillary column, remarkable stress is applied to a gel located on an end of the capillary column due to heat generation or the like to hinder injection of the sample into the capillary column, leading to such bad influence that the number of bases separable in migrational separation is limited. Furthermore, if the high voltage is abruptly applied, the gel may be forced out from the end of the capillary column due to electroosmosis flow. If the forced-out gel is damaged, the migrational separation state is disadvantageously deteriorated.

In slab gel electrophoresis, a large molecule (referred to as a macromolecule) such as template DNA having a size unreceivable in a gel matrix does not enter the gel matrix part but remains on an inlet for the gel matrix part Even if force moving the macromolecule by driving force of an electric field is applied to a separation part in slab gel electrophoresis, the separation part has sufficient resistance against this force due to its sufficient volume to hardly become a problem. Also, in capillary electrophoresis, a macromolecule does not enter a gel matrix part but remains on an inlet for the gel matrix part (this phenomenon is referred to as clogging). Capillary electrophoresis has the following features: 1) the volume of a separation carrier is extremely small, 2) the material for the separation carrier is not a strong one such as an acrylamide gel but a viscous polymer solution, and 3) electric field strength per unit length is large. Therefore, force moving the macromolecule by driving force of an electric field is large, and resistance against this force is small. Thus, occurrence of clogging results in deterioration of a separation pattern.

In DNA sequence determination, since a macromolecule in a sample is template DNA, in order to solve the aforementioned problem resulting from clogging, therefore, the template DNA must be removed before injecting the sample into a capillary column. It is possible to remove the template DNA by chemical pretreatment For example, when preparing a DNA fragment sample by the Sanger's method, an enzyme, antigen or antibody is bonded to a primer for separating the DNA fragment sample from a template by enzyme reaction or antigen-antibody reaction after preparing the sample. However, such chemical pretreatment is troublesome and requires much labor and time.

SUMMARY OF THE INVENTION

The first objective of the present invention is to provide a multi-capillary electrophoretic apparatus simplifying sample injection.

The second objective of the present invention is to provide, in relation to a capillary electrophoretic apparatus, a sample injection method and an apparatus suppressing deterioration of migrational separability.

In order to attain the first objective of simplifying sample injection of a multi-capillary electrophoretic apparatus, a specific sample plate is employed in the present invention. The sample plate comprises a disposable insulating resin base plate including one or a plurality of holes formed as wells having open bottom portions projecting flush with each other, and an electrode plate of conductive metal including cavities having smaller sizes than the wells formed on positions corresponding to two-dimensional arrangements of the wells formed by arrangement of the base plate for receiving press-fitted bottom portions of the wells thereby fixing the base plate. The wells of the base plate are press-fitted in and fixed to the cavities of the electrode plate to form spaces for receiving samples, and the samples are introduced into the wells respectively.

Such a base plate is disposable and hence can prevent contamination. The base plate may comprise only a single well, "n" number of wells aligned with each other, or wells two-dimensionally arranged in "n" number of rows and "m" number of columns. The material for forming the base plate is suitably prepared from universal engineering plastic such as polypropylene or polyethylene having chemical resistance and exceptional formability, in consideration of the disposability.

When employing this sample plate, voltage application to a plurality of wells becomes possible without employing a complicated electrode wiring structure. Sample injection into capillary columns of an electrophoretic apparatus employing a multi-capillary array having a number of capillary columns especially becomes simplified.

In a multi-capillary electrophoretic apparatus according to the present invention employing this sample plate, two-dimensionally arranged capillary column ends are downwardly set on a sample injection side of a mulb-capillary array migration part, the aforementioned sample plate having two-dimensionally arranged wells storing samples and a migration reservoir storing a migration buffer solution for applying a voltage to all capillary columns are arranged under the capillary column ends in correspondence to the arrangement of the capillary column ends, and the sample plate and the migration reservoir are movable for switching and bringing either one of these into contact with the capillary column ends.

In the multi-capillary electrophoretic apparatus, the samples are introduced into the wells of the sample plate fixed to the electrode plate in sample injection into the capillary columns, and the sample plate is moved by the moving mechanism for dipping ends of the respective capillary columns in the samples stored in the wells. Thereafter a voltage is applied between the electrode plate of the sample plate and other ends of the capillary columns and the samples are electrophoretically injected into the capillary columns. After sample injection, the sample plate is separated from the ends of the capillary columns by the moving mechanism, and the ends of the capillary columns are dipped into the buffer solution contained in the migration reservoir. Thereafter a voltage is applied between buffer solutions in reservoirs on both ends of the capillary columns thereby performing migration. Thus, operations from sample injection into the capillary columns to migration are automatically performed.

In this way, the multi-capillary electrophoretic apparatus employing the aforementioned sample plate according to the present invention for sample injection and comprising the moving mechanism switching and bringing either the sample plate or the migration reservoir into contact with the capillary column ends can automatically perform operations of sample injection into the capillary columns and migration.

A method according to the present invention for attaining the second objective of suppressing deterioration of migrational separability is adapted to control voltage application at the time of injecting a sample into a capillary column with voltage application to gradually raise the voltage when starting voltage application and gradually lower the voltage when finishing voltage application. As an apparatus, an applied voltage control part controlling voltage application in the aforementioned manner is provided.

Thus, stress of a gel located on a capillary column end can be reduced by suppressing abrupt heat generation and reduction. Furthermore, generation of large electroosmosis flow can be suppressed for preventing the gel from being forced out from the capillary column end. Consequently, migrational separability can be improved.

Another inventive method for attaining the second objective is a method of providing a separation carrier for preliminary separation between a sample and an end of a capillary column, injecting the sample into the capillary column through the preliminary separation carrier and removing the preliminary separation carrier before starting electrophoresis.

A capillary electrophoretic apparatus according to the present invention for carrying out the sample injection method comprises a preliminary separation part storing a separation carrier for preliminary separation and a sample so that the preliminary separation carrier is located between an end of an inserted capillary column and the sample.

In the sample injection method provided with the preliminary separation part, a voltage is applied in preliminary separation so that the sample starts moving toward the end of the capillary column. At this time, a macromolecule contained in the sample also starts moving toward the end of the capillary column and causes clogging on the preliminary separation carrier. At the same time, a target of analysis contained in the sample other than the macromolecule passes through the preliminary separation carrier and moves toward the end of the capillary column. When the target of analysis enters the capillary column, the preliminary separation carrier is removed and thereafter the target of analysis is separated. Thus, the macromolecule unreceivable in the separation carrier charged in the capillary column is removed in the stage of preliminary separation. Due to this, no macromolecule exists in separation analysis, and a separation pattern can be prevented from deterioration resulting from clogging.

The foregoing and other objects, features, aspects and advantages of the present invention will become more apparent from the following detailed description of the present invention when taken in conjunction with the accompanying drawing.

DESCRIPTION OF THE PREFERRED EMBODIMENTS

FIGS. 1A to 3 show an embodiment of the present invention attaining the first objective of simplifying sample injection in a multi-capillary electrophoretic apparatus.

Figure 1A:
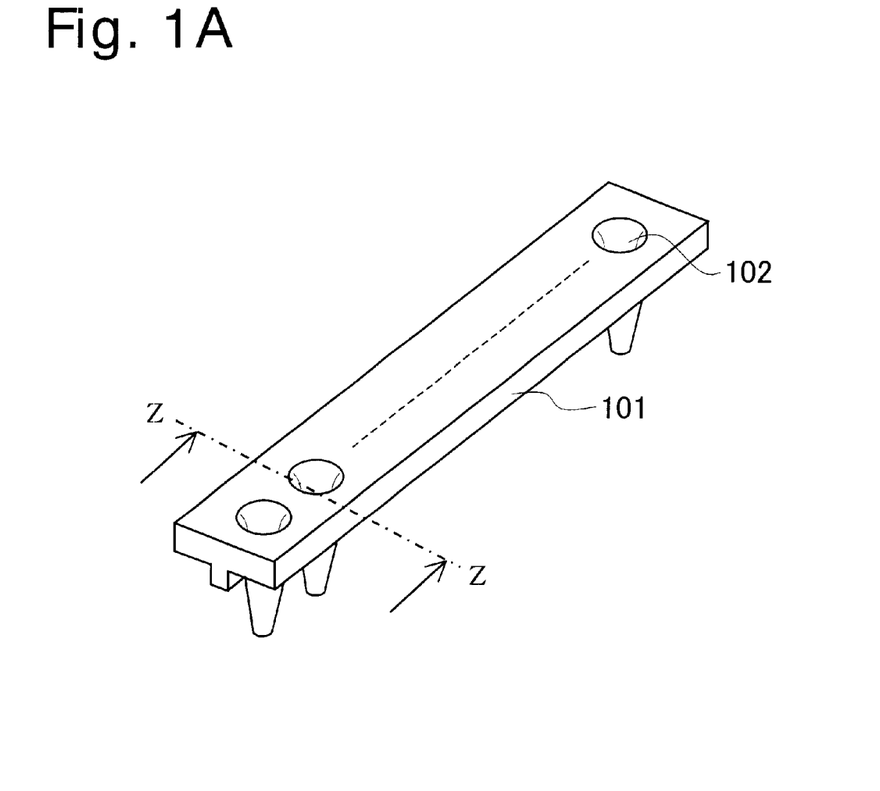
FIG. 1A is a schematic perspective view showing an exemplary base plate used in a sample plate according to an embodiment of the present invention.
Figure 1B:
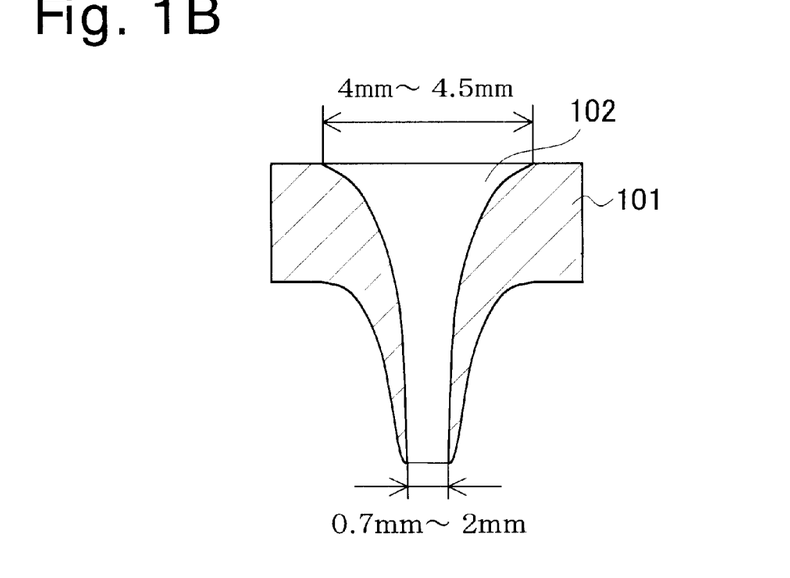
FIG. 1B is a sectional view taken along the line Z—Z in FIG. 1A.

FIG. 1A is a perspective view showing a base plate 101 in a sample plate 100 according to the embodiment employed in the present invention. FIG. 1B is a sectional view taken along the line Z—Z in FIG. 1A. The base plate 101 is entirely formed by a thin plastic material, and wells 102 of holes having open bottom portions are arranged on its flat surface at regular intervals. Each well 102 has a thin bottom portion coming into contact with an electrode plate 104 and a thick upper portion receiving a capillary column. The sizes of the open bottom portion and the open upper portion are 0.7 mm to 2 mm and 4 mm to 4.5 mm respectively. Thus, when the open bottom portion is closed with the electrode plate 104 as described later for storing a sample, the level can be raised even if the amount of the sample is small while the capillary column can be readily guided into the sample stored in the well 102.

Figure 2A:
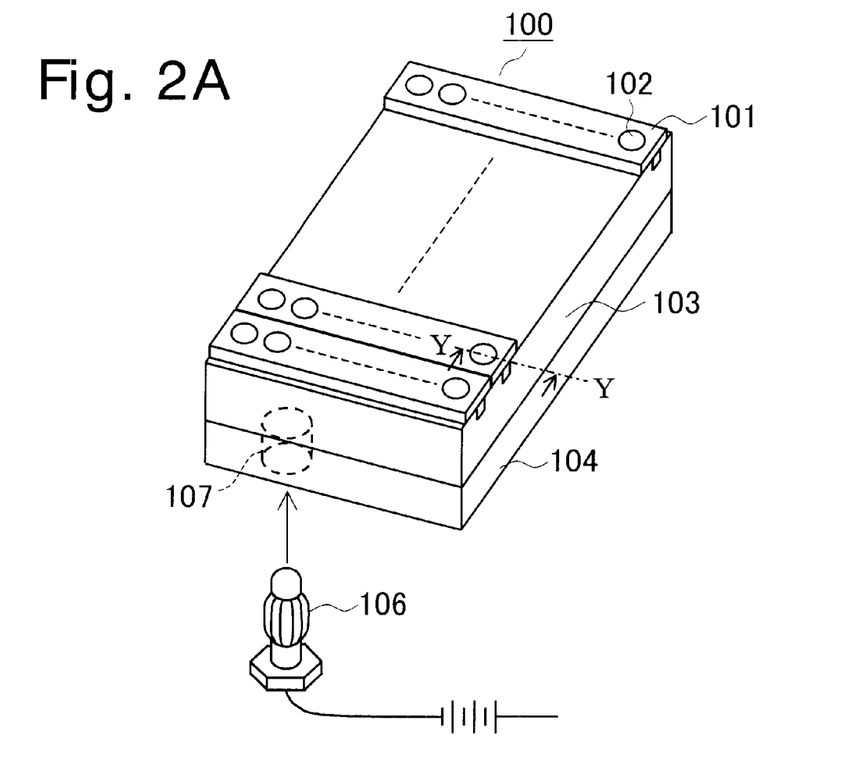
FIG. 2A is a schematic perspective view showing the sample plate according to the embodiment.
Figure 2B:
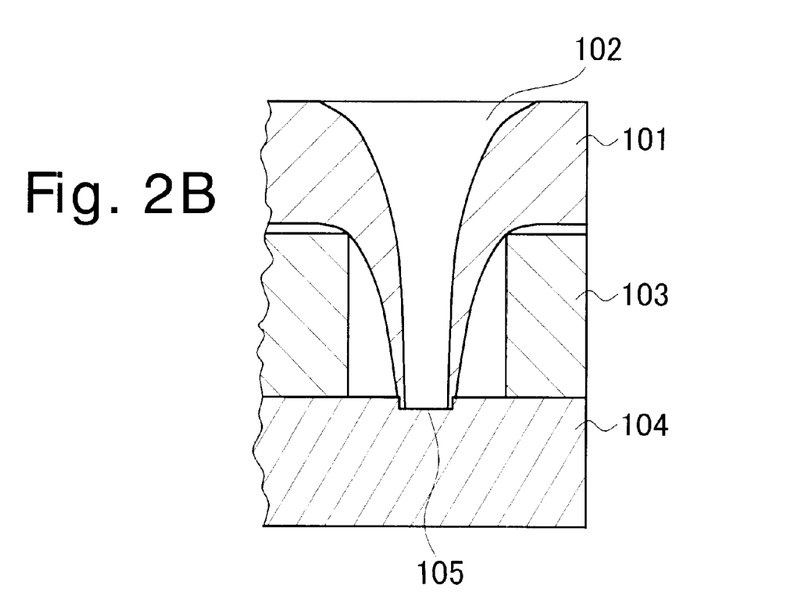
FIG. 2B is a sectional view taken along the line Y—Y in FIG. 2A.

FIG. 2A is a perspective view showing the sample plate 100 according to this embodiment. FIG. 2B is a sectional view taken along the line Y—Y in FIG. 2A.

The electrode plate 104 is made of a conductive material such as stainless steel having high mechanical strength, and vertically and horizontally arranged cavities 105 are formed on its flat surface. A plurality of base plates 101 are arranged on the surface of the electrode plate 104. The arrangement of the cavities 105 corresponds to two-dimensional arrangement of the wells 102 of the base plates 101 arranged on the surface of the electrode plate 104. The size of each cavity 105 is slightly smaller than the outer size of the bottom portion of each well 102, for fixing each base plate 101 by press-fitting and engaging the bottom portion of each well 102 into each cavity 105. A migration high voltage line connection hole 107 is formed on the bottom portion of the electrode plate 104 to be connected with a high voltage power source through a plug 106 set on the body of the electrophoretic apparatus. A well guide 103 guiding the wells 102 into the cavities 105 of the electrode plate 104 is fixed to the surface of the electrode plate 104, and through holes are formed on positions corresponding to the cavities 105. The well guide 103 may be made of any material such as a conductor or an insulator. The base plates 101, the well guide 103 and the electrode plate 104 form the sample plate 100.

After use, the electrode plate 104 is detached from the base plates 101. While the base plates 101 are discarded after single use, the electrode plate 104 and the well guide 103 are repeatedly used. The electrode plate 104 is washed for reuse. In particular, the cavities 105 having portions coming into contact with samples are necessarily washed for reuse.

The sample plate 100, which can be used not only in a gel electrophoretic apparatus having capillary columns charged with gels such as polyacrylamide gels, linear acrylamide gels or polyethylene oxide gels as separation media but also in a capillary zone electrophoretic apparatus performing free migration in capillary columns charged with no gels, is applicable to any electrophoretic apparatus so far as the same employs a plurality of capillary columns.

Figure 3:
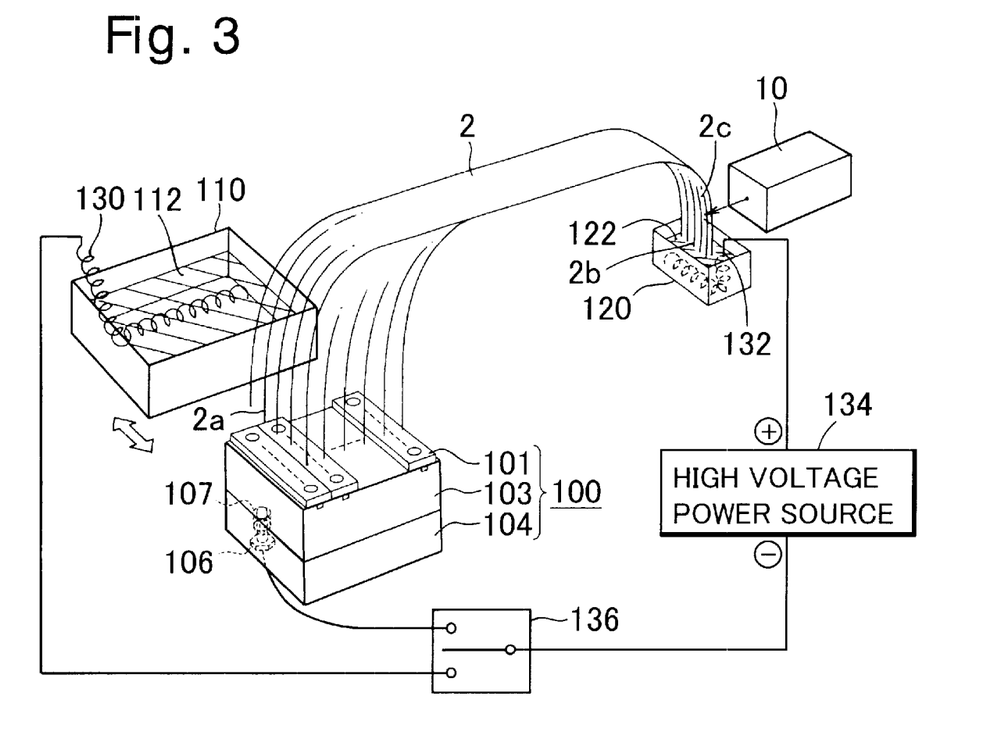
FIG. 3 is a schematic perspective view showing an embodiment of a multi-capillary electrophoretic apparatus performing sample injection with the sample plate of the embodiment.

FIG. 3 schematically shows an embodiment of a multi-capillary electrophoretic apparatus performing sample injection with the sample plate 100 and thereafter performing migrational separation of samples.

A pair of reservoirs 110 and 120 store buffer solutions 112 and 112 respectively, and electrodes 130 and 132 are provided in the buffer solutions 112 and 122 respectively. The sample plate 100 is that shown in FIG. 2A. Samples are introduced into the respective wells 102 of the sample plate 100, and a high-tension distribution cable is connected to the plug 106.

A high voltage switching part 136 switchably connects the reservoir 110 and the sample plate 100 so that wiring can be switched, and a high voltage power source 134 is connected between the high voltage switching part 136 and the electrode 132 provided in the other reservoir 120. The high voltage power source 134 is connected with an applied voltage control part (not shown) control applied voltages and times for sample injection and migration.

One capillary column ends 2a of a capillary array 2 are inserted one by one in the respective wells 102 of the sample plate 100 in sample injection, while the reservoir 110 is switched to and arranged on the position of the sample plate 100 after sample injection, so that the one ends 2a of the capillary array 2 are dipped in the buffer solution 112. The other ends 2b of the capillary array 2 are dipped in the buffer solution 122 in the other reservoir 120. The other ends 2b are provided with detected portions 2c irradiated with measuring light or excitation light from an optical measuring part 10 detecting the samples by absorbance or fluorescence.

The capillary array 2 has two-dimensional arrangement corresponding to the arrangement of the wells 102 of the sample plate 100 on the side of the one ends 2a while capillary columns are aligned with each other on the detected portions 2c so that the arrangement surfaces of the capillary columns are perpendicularly irradiated with the measuring light or the excitation light.

Each capillary column forming the capillary array 2 is made of quartz glass or borosilicate glass (e.g., Pyrex) and has an outer diameter of 200 to 300 μm and an inner diameter of 75 to 100 μm. The outer periphery of the capillary column is preferably covered with a film of a non-fluorescent material such as $SiO_2$ generating no fluorescence by excitation light from ultraviolet to near infrared regions or generating fluorescence to an extent not hindering fluorescence measurement In this case, the film may not be removed on the detected portion 2c. If the capillary column has a resin film generating fluorescence, the film is removed on the detected portion 2c. A plurality of such capillary columns are arranged in the capillary array 2.

The capillary columns are charged with polyacrylamide gels, linear acrylamide gels or polyethylene oxide (PEO) gels as gels of separation media. Samples containing four types of DNA fragments labeled by four types of fluorescent materials selected from FAM, JOE, TAMRA, ROX, R6G, R-110 and the like varying with end bases or labeled in four types by at least two types of fluorescent materials at different ratios are injected into the capillary columns respectively and simultaneously electrophoresed.

The sample plate 100 and the reservoir 110 are so switched and arranged by a moving mechanism (not shown in FIG. 3) that either one thereof selectively comes into contact with the one ends 2a of the capillary array 2 as indicated by the broad arrow in FIG. 3.

The wells 102 not only store already treated samples, but also can be so employed that sample injection can be performed by treating samples by a PCR (polymerase chain reaction) method through the wells 102 and thereafter inserting the one capillary column ends 2a of the capillary array 2 into the samples stored in the wells 102. The PCR method is a method of remarkably amplifying only one target part of DNA. In the PCR method, a primer is added to a sample of DNA, the temperature is raised to dissociate double-stranded DNA to single chains. Then the temperature is lowered to bond the primer with the DNA chains, the temperature is slightly raised to synthesize DNA, and the temperature is further raised to form single-stranded DNA The operation of changing the temperature upward and downward is repeated thereby amplifying/synthesizing prescribed part of DNA in a large quantity.

The electrode plate 104 of the sample plate 100 shown in FIG. 2A is set on the body of the electrophoretic apparatus, while the plug 106 is inserted into the migration high voltage line connection hole 107 and connected to the high-tension distribution cable. The wells 102 of the base plates 101 are inserted into the through holes of the well guide 103 and further press-fitted and engaged into the cavities 105 of the base plates 101 for fixing the base plates 101 to the electrode plate 104. Thereafter the samples are introduced into the wells 102 of the base plates 101. If necessary, centrifugal defoaming is lightly performed so that the samples come into contact with the electrode plate 104.

In sample injection, the capillary column ends 2a on the side of the one end of the capillary array 2 are dipped one by one in the samples stored in the wells 102 of the sample plate 100 while the other ends of the capillary columns are collectively dipped in the buffer solution 122 stored in the reservoir 120. A high voltage is simultaneously applied to all wells 102 through the electrode plate 104 for injecting the samples into the capillary columns.

After sample injection, high voltage application is temporarily stopped and the moving mechanism moves the sample plate 100 and the reservoir 110, thereby dipping the capillary column ends on the side of the samples (the side of the one capillary column ends 2a of the capillary array 2) into the buffer solution 11 2 stored in the reservoir 110. Thereafter, a high voltage is applied between the reservoirs 110 and 120 for performing electrophoretic separation. In order to connect a high voltage line to the electrode plate 104, a plate spring or the like connected with the high voltage power source 136 may be provided on a position for fixing the sample plate 100 so that the plate spring comes into contact with the electrode plate 104 when fixing the sample plate 100. The moving mechanism may move the sample plate 100 and the reservoir 10 in a horizontal plane for vertically moving the one capillary column ends 2a of the capillary array 2.

The number of the wells 102 of the sample plate 100 can be arbitrarily set in response to the number of the capillary columns.

Figure 5:
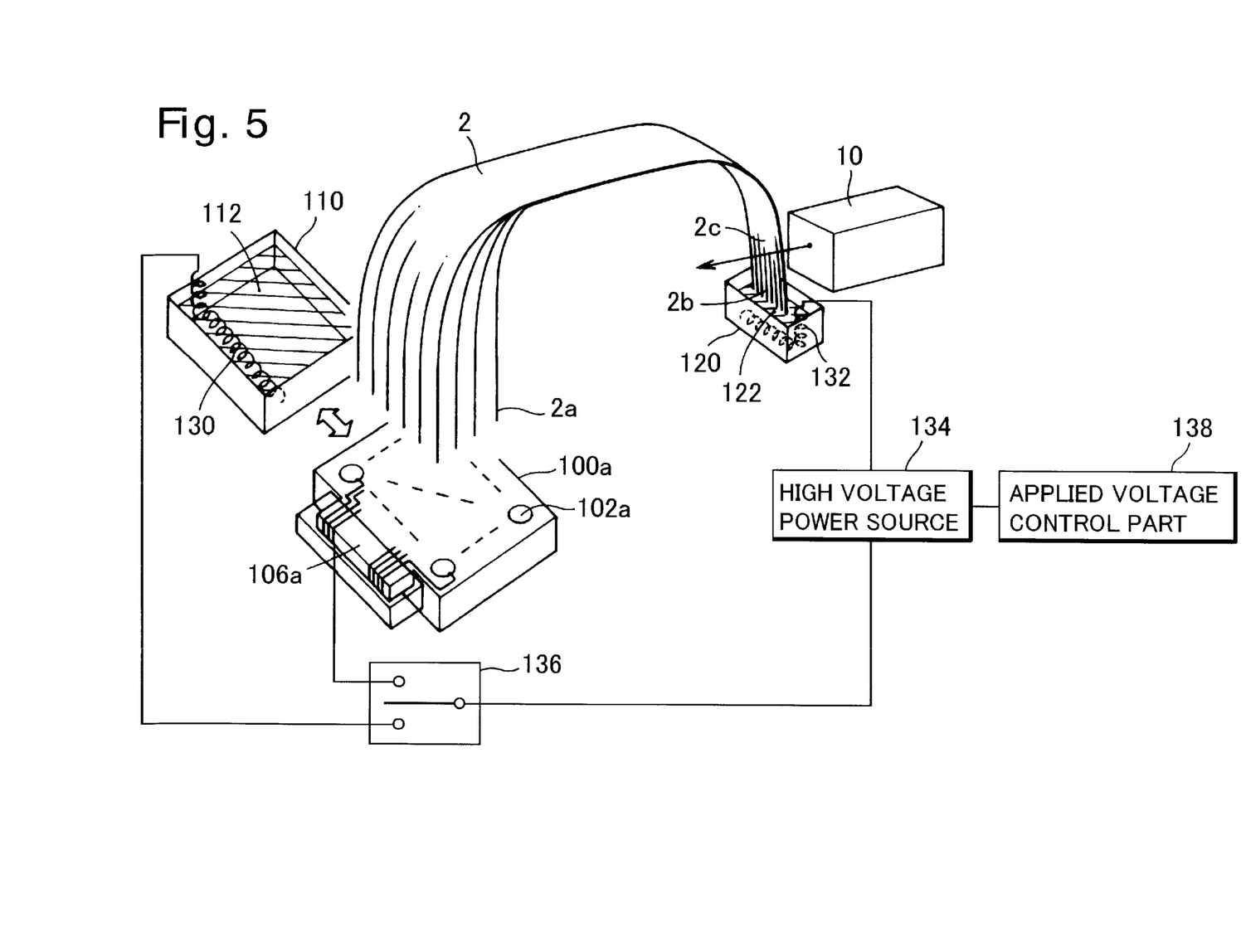
FIG. 5 is a schematic perspective view showing a multi-capillary electrophoretic apparatus according to another embodiment of the present invention.

FIG. 5 is a schematic perspective view showing an embodiment of a capillary electrophoretic apparatus to which the present invention for attaining the second objective of suppressing deterioration of migrational separability is applied. While a multi-capillary electrophoretic apparatus is shown, the present invention is also applicable to a capillary electrophoretic apparatus comprising a single capillary column.

A sample plate 100a, made of an insulating material, comprises a flat surface and a connector portion 106a connected with the same. A plurality of wells 102a are vertically and horizontally arranged on the surface of the sample plate 100a at regular intervals. The wells 102a are bottomed holes, and individual electrode patterns reaching the connector portion 106a from the bottoms through the base plate surface are formed on the respective wells 102a. Samples are introduced into the respective wells 102a of the sample plate 100a, and a high-tension distribution cable is connected to the connector portion 106a.

The structure of this electrophoretic apparatus other than the sample plate 100a is identical to that of the capillary electrophoretic apparatus shown in FIG. 3, and hence redundant description is omitted. An applied voltage control part 138 connected with a high voltage power source 134 for controlling applied voltages and times for sample injection and migration is implemented by a microcomputer or the like.

The one capillary column ends 2a of a capillary array 2 are inserted one by one in the respective wells 102a of the sample plate 100a in sample injection, while the sample plate 100a and a reservoir 110a are switched after sample injection so that the one capillary column ends 2a are dipped into a buffer solution 112. The other ends 2b of the capillary array 2 are dipped into a buffer solution 122 stored in another reservoir 120.

Operations of this embodiment shall now be described.

Samples are introduced into the wells 102a of the sample plate 100a respectively. Thereafter the one capillary column ends 2a of the capillary array 2 are dipped one by one into the samples stored in the wells 102a of the sample plate 100a, while the other ends 2b of the capillary array 2 are collectively dipped in the buffer solution 122 stored in the reservoir 120. The wells 102a are connected with a high voltage power source 134 through a high voltage switching part 136, the connector portion 106a and an electrode pattern. A high voltage is applied between the wells 102a and the buffer solution 122 by the high voltage power source 134, for injecting the samples into capillary columns. At this time, the applied voltage control part 138 controls the applied voltage and the time.

Figure 6:
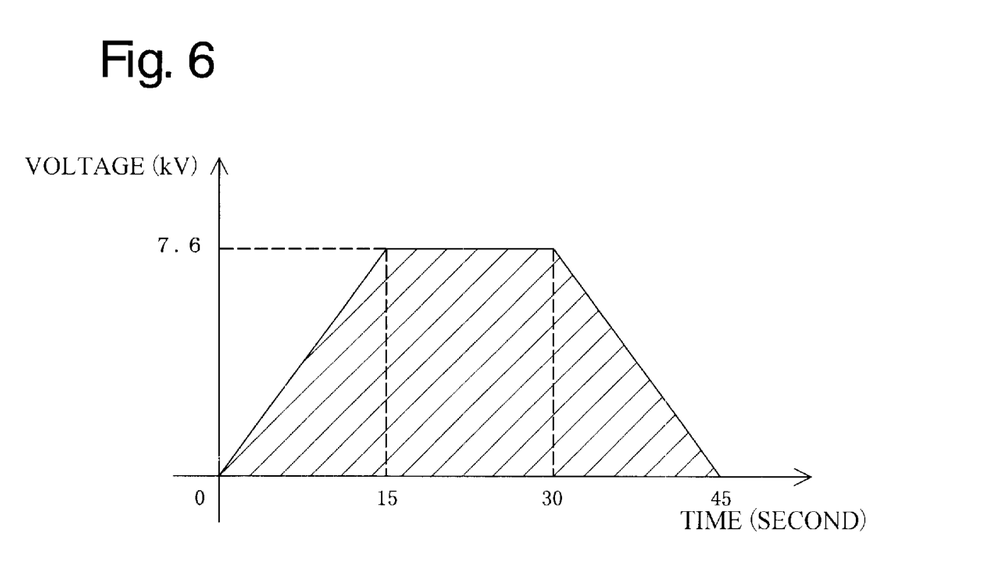
FIG. 6 illustrates examples of a voltage applied in sample injection controlled by an applied voltage control part of the embodiment and time, with the vertical and horizontal axes showing the voltage (kV) and the time (sec.) respectively.

FIG. 6 illustrates examples of the voltage applied in sample injection and the time controlled by the applied voltage control part 138. The horizontal and vertical axes show the voltage (kV) and the time (sec.) respectively. The applied voltage control part 138 controls the high voltage power source 134, for gradually raising the voltage to reach 7.6 kV after a lapse of 15 seconds from start of sample injection. Thereafter the voltage of 7.6 kV is applied for 15 seconds. Then, the voltage is lowered from 7.6 kV to 0 V over 15 seconds, and voltage application in sample injection is terminated. An integrated value (area of the slant line part) of the product of the applied voltage and the time is set to be equal to an integrated value (area of the slant line part) of the product of the applied voltage and the time shown in FIG. 4. The applied voltage and the time vary with the types of the samples or the type of the apparatus, and hence the integrated value thereof varies with the types of the samples or the type of the apparatus.

Abrupt heat generation and reduction in gels in the capillary columns can be suppressed by controlling the applied voltage and the time in the aforementioned manner, for relaxing stress on the gels located on capillary column ends. Furthermore, it is also possible to suppress occurrence of large electroosmosis flow and prevent the gels from being forced out from the capillary column ends. In addition, it is also possible to suppress overshoot of a current resulting from abrupt application of the high voltage. After sample injection, the moving mechanism moves the sample plate 100*a* and the reservoir 110 thereby dipping the one ends 2*a* of the capillary array 2 on the side of the samples into the buffer solution 112 stored in the reservoir 110. Thereafter a high voltage is applied between the reservoirs 110 and 120 for performing electrophoretic separation. A power supply voltage for migration is for example, 30 kV, and a current capacity is 10 to 30 mA. Migrational separability, which is about 100 bases in general, can be improved to 200 to 300 bases by injecting the samples into the capillary columns in the aforementioned manner.

The reservoir 110 may also have a plurality of wells storing buffer solutions similar to the sample plate 100*a* so that independent voltages can be applied to the respective wells by providing individual electrode patterns on the respective wells for simultaneously performing electrophoresis under different conditions.

Figure 7A:
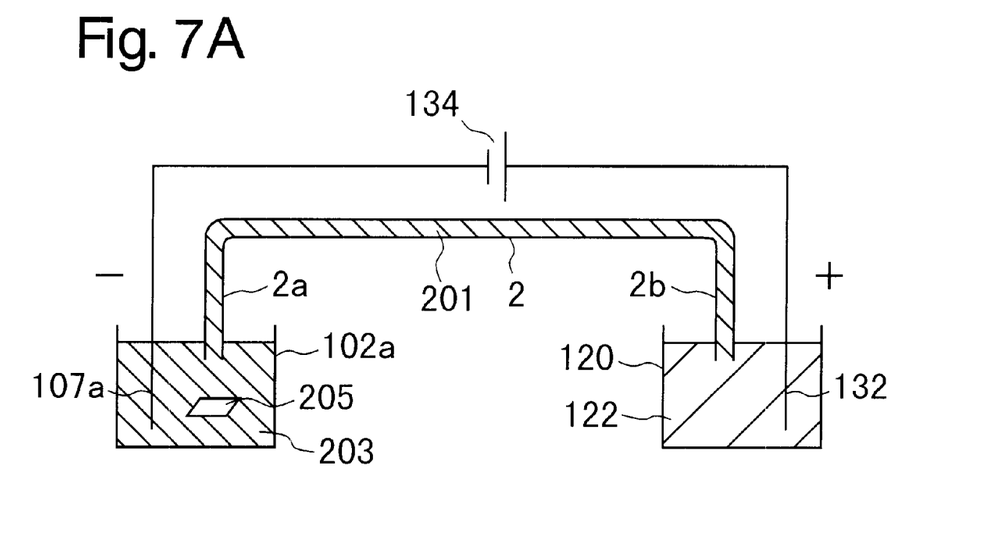
FIG. 7A conceptually illustrates an operation in sample injection of an embodiment preventing deterioration of a separation pattern resulting from clogging in relation to a single capillary column.

FIG. 7A conceptually illustrates an operation in sample injection of an embodiment for preventing deterioration of a separation pattern resulting from clogging in relation to a single capillary column. A capillary electrophoretic apparatus to which this embodiment is applied is not restricted to that shown in FIG. 5 but the multi-capillary electrophoretic apparatus shown in FIG. 3 or still another capillary electrophoretic apparatus is also employable. The following description is made with reference to the multi-capillary electrophoretic shown in FIG. 5 as an example.

The sample plate 100*a* defines a preliminary separation part serving also as a sample injection part A fluid gel (separation carrier for preliminary separation) 203 and a sample 205 adsorbed by filter paper are contained in each well 102*a* of the preliminary separation part 100*a* so that the gel 203 is interposed between a capillary column 2 and the sample 205. A wiring pattern is formed on the preliminary separation part 100*a* and an electrode 107*a* is inserted in each well 102*a*, while the electrode 107*a* is connected to a high-tension distribution cable through the connector portion 106*a*. Although the electrode 107*a* is shown as a wire, it is formed as a thin-film pattern extending from the surface of the preliminary separation part 100*a* to the well 102*a*.

The capillary column 2 forming a capillary array is charged with a fluid gel (separation carrier) 201 identical to the gel 203. The one end 2*a* of the capillary column 2 is inserted in each well 102*a* of the preliminary separation part 100*a* in sample injection and then dipped into the buffer solution 112 stored in the reservoir 110 after sample injection. The other end 2*b* of the capillary column 2 is dipped into the buffer solution 122 stored in the other reservoir 120, and irradiated with measuring light or excitation light from the optical measuring part 10 detecting the sample 205 by absorbance or fluorescence.

The gels 201 and 203 can be prepared by fluid gels consisting of 2% HEC (hydroxyethyl cellulose: product by Polyscience Co., Ltd. (U.S.A.), 7M urea or ×1 TBE (tris borate buffer). In this embodiment, the gels 201 and 203 are the same, but they do not have to be.

The operations of this embodiment shall now be described with reference to FIGS. 5, 7A and 7B.

In sample injection, the one ends 2*a* of the capillary columns are dipped one by one into the gels 203 stored in the wells 102*a*, while the other ends 2*b* of the capillary columns are collectively dipped into the buffer solution 122 stored in the reservoir 120. The high voltage switching part 136 is connected to the preliminary separation part 100*a* for applying a high voltage between each well 102*a* and the reservoir 120 by the high voltage power source 134 for electrophoresis (FIG. 7A).

A target of analysis such as DNA contained in each sample 205 starts moving toward each capillary column 2. At this time, a macromolecule such as template DNA simultaneously starts to move, but cannot enter a matrix of the gel 203 and causes clogging, and remains on a boundary surface between the gel,203 and the sample 205. At the same time, the target of analysis passes through the gel 203 and moves toward the gel 201 in the capillary column 2, and the sample 205 is injected.

After injection of the object of analysis, high voltage application is temporarily stopped and the moving mechanism moves the preliminary separation part 100*a* and the reservoir 110 thereby dipping the one end 2*a* of the capillary column 2 on the side of the sample 205 into the buffer solution 112 stored in the reservoir 110. Thereafter a high voltage is applied between the reservoirs 110 and 120 for performing electrophoretic separation (FIG. 7B). At this time, the injected sample 205 does not contain macromolecule, and hence deterioration of a separation pattern does not occur by clogging. The voltage for sample injection into the capillary column 2 and power supply voltage for migration are for example, 30 kV, and current capacity is 10 to 30 mA.

Figure 8:
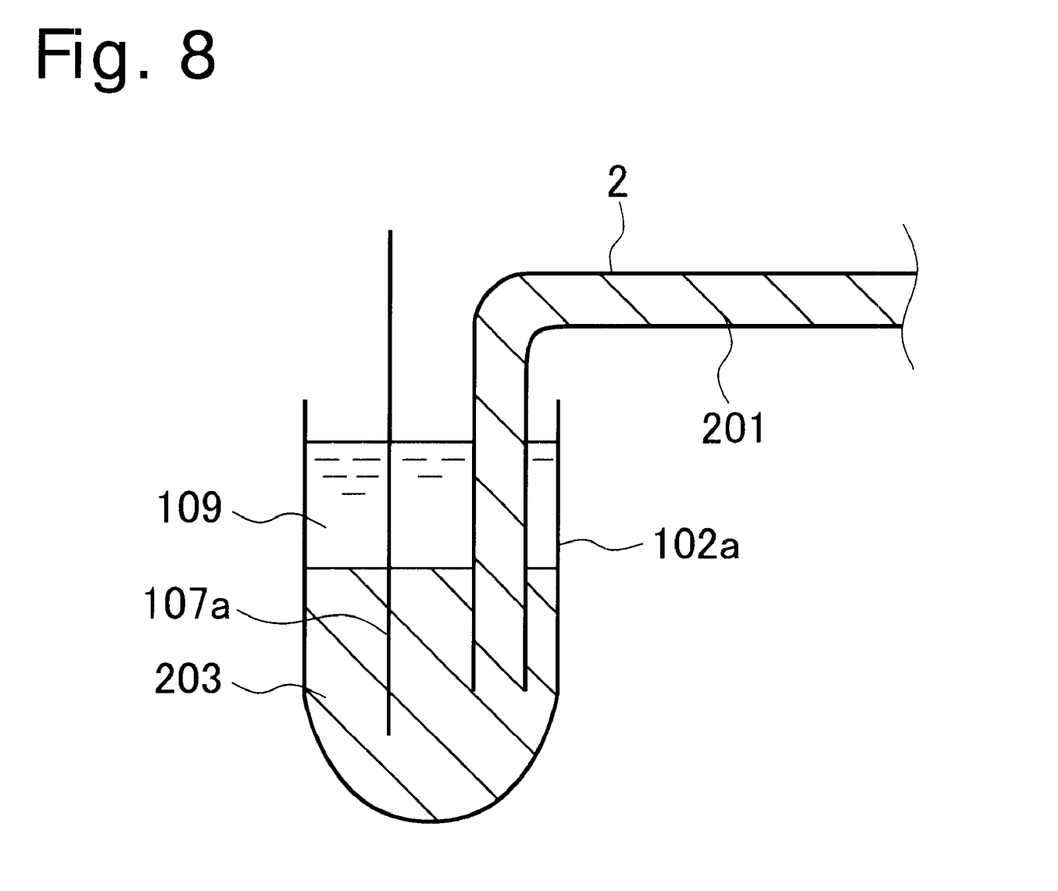
FIG. 8 is a schematic diagram showing another way of introducing a sample in the embodiment

FIG. 8 is a schematic diagram showing another sample injection method in this embodiment A sample is generally prepared as an aqueous solution. Therefore, an aqueous solution 109 containing a sample and a gel 203 are stratified in a well 102*a*. The gel 203 has higher density than the aqueous solution 109, and hence the aqueous solution 109 can be stratified as an upper layer.

One capillary column ends 2*a* of a capillary array 2 are inserted into the gel 203 and a voltage for sample injection is applied, so that a macromolecule in the sample contained in the aqueous solution 109 causes clogging and remains on the interface between the aqueous solution 109 and the gel 203 while the object of analysis passes through the gel 203 and is injected into the capillary column.

The number of wells of a preliminary separation part 100a can be arbitranily set in response to the number of capillary columns.

It is also preferable to enable automatic performance of the aforementioned operations.

Figure 7B:
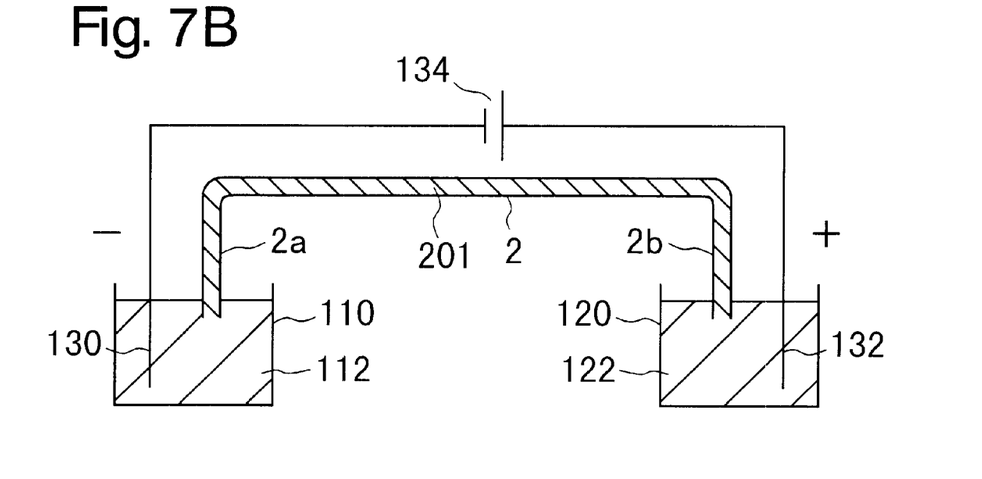
FIG. 7B conceptually illustrates later migrational separation.

The sample injection methods described with reference to FIGS. 6 to 8 are also applicable to the capillary electrophoretic apparatus shown in FIG. 3 employing the sample plate shown in FIG. 2A, if the capillary columns are charged with gels.

Although the present invention has been described and illustrated in detail, it is clearly understood that the same is by way of illustration and example only and is not to be taken by way of limitation as the spirit and scope of the present invention are limited only by the terms of the appended claims.

What is claimed is:

1. A sample plate comprising:

a disposable insulating resin base plate including one or a plurality of holes formed as wells having open bottom portions projecting flush with each other; and an electrode plate of conductive metal including having smaller sizes than the wells, formed on positions corresponding to two-dimensional arrangement of the wells formed by the base plate, whereby the bottom portions of the wells are press-fittable into the cavities of the electrode plate, thereby fixing the base plate to the electrode plate.

2. The sample plate in accordance with claim 1, wherein the base plate is a strip-shaped one including a plurality of the wells aligned with each other, and a plurality of the base plates are aligned with each other thereby forming the two-dimensional arrangement of the wells.

3. The sample plate in accordance with claim 1, further comprising:

a well guide, arranged between the base plate and the electrode plate, having through holes on positions corresponding to the cavities of the electrode plate.

4. A multi-capillary electrophoretic apparatus comprising:

a multi-capillary migration part including a plurality of capillary columns, having two-dimensionally arranged capillary column ends downwardly directed on a sample injection side so that a plurality of samples are injected one by one into the capillary columns and simultaneously electrophoresed in all the capillary columns;

an optical measuring part irradiating the capillary columns with light on the multi-capillary array migration part for measuring absorbance by the samples or fluorescence from the samples on irradiated portions;

a sample plate comprising a disposable insulating resin base plate, arranged under the capillary column ends of the multi-capillary array migration part on the sample injection side, including wells for storing samples, two-dimensionally arranged in correspondence to arrangement of the capillary column ends, having open bottom portions projecting flush with each other and an electrode plate of conductive metal including cavities having smaller sizes than the wells formed on positions corresponding to two-dimensional arrangement of the wells formed by arrangement of the base plate, whereby the bottom portions of the wells are press-fittable into the cavities of the electrode plate, thereby fixing the base plate to the electrode plate;

a migration reservoir storing a migration buffer solution for applying a voltage to all the capillary columns; and wherein the sample plate and the migration reservoir are movable for switching and bringing either one of these into contact with the capillary column ends.

* * * * *